United States Patent [19]

Thorner

[11] Patent Number: 5,036,045

[45] Date of Patent: Jul. 30, 1991

[54] METHOD FOR INCREASING GROWTH HORMONE SECRETION

[75] Inventor: Michael O. Thorner, Charlottesville, Va.

[73] Assignee: The University of Virginia Alumni Patents Foundation, Charlottesville, Va.

[21] Appl. No.: 245,269

[22] Filed: Sep. 16, 1988

Related U.S. Application Data

[63] Continuation of Ser. No. 775,249, Sep. 12, 1985, abandoned.

[51] Int. Cl.⁵ ............................................... A61K 37/36
[52] U.S. Cl. .......................................... 514/12; 514/964
[58] Field of Search ................................... 514/12, 964

[56] References Cited

U.S. PATENT DOCUMENTS 4,526,938  7/1985  Churchill ............................ 525/435
4,617,149  10/1986  DiMarchi ........................ 435/172.3

OTHER PUBLICATIONS

Clark et al., *Nature*, 314, 281-283 (1985).
Ceda et al., *Endocrinology*, vol. 116, No. 1334-1340 (1985).

*Primary Examiner*—F. T. Moezie
*Attorney, Agent, or Firm*—Oblon, Spivak, McClelland, Maier & Neustadt

[57] ABSTRACT

A method for increasing growth hormone secretion or inducing the biologic effects of growth hormone by continuous administration of growth hormone releasing factor or analog thereof is disclosed.

1 Claim, No Drawings

METHOD FOR INCREASING GROWTH HORMONE SECRETION

The Government has rights in this invention pursuant to NIH Grant AM 32632 and NIH Grant GCRC RR 841.

This is a continuation of application Ser. No. 06/775,249, filed Sept. 12, 1985, now abandoned.

BACKGROUND OF THE INVENTION

1. Field of the Invention

The present invention relates to increasing growth hormone secretion and/or the biologic effects of growth hormone.

2. Discussion of the Background

The therapeutic administration of hormones—substances that act at sites distant from the location of release—has heretofore been subject to the technical limitations of pharmacology. In general, the pharmacological administration of hormones has meant virtually instant introduction of a large dose of an active agent. This is clearly contrary to the physiological nature of release which consists of small amounts released as required by a particular organism.

The dichotomy between pharmacology and physiology is commonly noted in insulin use. Normal subjects release insulin as needed. High amounts may be released when food is eaten, but chronic low levels remain available in times of reduced but not negligible demand. Diabetic subjects receive an approximated insulin dosage in about 1 to 3 injections daily with only minimal accommodation possible for moment to moment insulin demands or insulin by pump supplemented with bolus injections.

A similar dichotomy is found with growth hormone. Growth hormone releasing factor is a hormone produced in the brain which stimulates the release of growth hormone from the pituitary. It has previously been shown in that the administration of growth hormone releasing factor stimulates growth hormone secretion from the pituitary of multiple different species from fish to man. The structure of human growth hormone releasing factor has previously been described and is made up of 40 or 44 amino acids (Rivier, J; Spiess, J; Thorner, M; Vale, W; Nature, 1982, 300, 276-278; Spiess, J; Rivier, J; Thorner, M; Vale, M; Biochemistry, 1982, 24, 6037-6040, and Guillemin, R; Brazeau, P; Bohlen, P; Esch, F; Ling, N; Science, 1982, 218, 585-587). Analogs of the peptide ranging from 29 amino acids or longer have also been shown to stimulate growth hormone secretion.

Growth hormone, like insulin, is also regulated by an inhibitory hormone produced by the hypothalamus called somatostatin. Studies in animals have suggested that growth hormone releasing factor desensitizes those cells which secreted growth hormone in response to the growth hormone releasing factor. Pharmaceutically administered Growth Releasing Factor has heretofore been believed to be effective only when administered in a discontinuous manner and over a length of time. As a matter of fact, one study on the normal rat indicates that pulsatile growth hormone releasing factor administration accelerates growth, while continuous administration of growth hormone releasing factor does not (Clark R, G; Nature, 1985, 314, 281-283). It has thus been considered necessary to give growth hormone releasing factor by pulsatile administration. Patients suffering from growth hormone deficiency have heretofore been given inconvenient and time consuming periodic injections of growth hormone releasing factor or growth hormone; typically by 2 to 3 times weekly injections for growth hormone or repeated injections per day for growth hormone releasing factor or pump pulsitile administration.

Accordingly, the existing methods of administering growth hormone releasing factor suffer the disadvantage of difficulty of patient compliance with the treatment, as well as pain or dangers associated with multiple administrations. Children especially do not like the treatment and are difficult to keep on administration schedule.

SUMMARY OF THE INVENTION

Accordingly, it is an object of the present invention to provide a method for effectively increasing growth hormone secretion or increasing the biologic effect of growth hormone.

It is another object of this invention to provide a method for the practical and convenient administration of growth hormone releasing factor or an analog thereof.

It is another object of this invention to provide a method for growth hormone releasing factor or an analog thereof without adverse effects to a patient.

Accordingly, it has now been suprisingly discovered that, in fact, the continuous administration of growth hormone releasing factor or an analog thereof does not suppress growth hormone secretion, and that thus all of the objects of this invention are satisfied with a novel method for increasing growth hormone secretion or for increasing the biologic effect of growth hormone in which growth hormone releasing factor or an analog thereof is administered continuously to a patient. This discovery is especially surprising in view of the fact that numerous hormone releasing factors suppress or stop hormone secretion when administered continuously. For example, with the well studied hypothalamic hormone Gonadotropin, when Gonadotropin releasing hormone is administered continuously Gonadotropic secretion ceases.

The present invention also provides a kit for the continuous administration of growth hormone releasing factor or an analog thereof.

DETAILED DESCRIPTION OF THE PREFERRED EMBODIMENTS

Prior to the present invention it was believed that growth hormone releasing factor would desensitize those cells which secreted growth hormone in response to growth hormone releasing factor. Growth hormone releasing factor has thus always been administered intermittently to patients suffering from growth hormone related problems. The present invention is based on the surprising discovery that a continuous infusion of growth hormone releasing factor or analog thereof leads to augmented growth hormone secretion and/or augmentation of the biologic effect of growth hormone. This discovery allows a delayed release preparation to be administered rather than giving growth hormone releasing factor injections several times a day or by pulsitile pump administration, or to give growth hormone by 2-3 times weekly injections. This discovery permits augmentation of growth hormone secretion and/or its biologic effects in all vertebrates (including animals, fish and man) both in the diseased state of growth hormone deficiency to restore normal growth hormone secretion or to increase growth hormone secretion above normal in vertebrates.

The growth hormone releasing factor or its analog may be administered at dosages ranging from 0.1 ng/kg/min to 1000 ng/kg/min, preferably in dosages ranging from 1.0 ng/kg/min to 100 ng/kg/min, to obtain constant levels of growth hormone releasing factor for a long period of time. For example, dosages of 1.0 ng/kg/min to 100 ng/kg/min for growth hormone releasing factor-40 (GFR-40) may be used. More potent analogs may be administered at lower dosages.

The levels of growth hormone releasing factor obtained may be from about 0.1 µg/ml to about 12 µg/ml, preferably about 0.2 µg/ml to 10 µg/ml.

Generally, all growth hormone releasing factors and their analogs have activity in varied organisms. The degree of activity varies from species to species, although. Any kind of growth hormone releasing factors or their analogs possessing activity in vertebrates may be used in this invention. Growth hormone releasing factors obtained by peptide synthesis, fermentation, natural sources, or a combination of these sources may be used. Examples of natural growth hormone releasing factors which may be used are rat hypothalamic growth hormone releasing factor, caprine growth hormone releasing factor or porcine growth hormone releasing factor or analogs thereof (synthetic and non-synthetic). For example, growth hormone releasing factors from any of the following vertebrates may be used: cow, sheep, horse, rat, mice, chicken, turkey, quail, trout, perch and man. Analogs of the growth hormone releasing factors are characterized by having peptide sequences which are part of the corresponding growth hormone releasing factor. By comparison to its parent growth hormone releasing factor, an analog may be part of the parent peptide sequence or it may be part of the parent peptide sequence in which up to 10 amino acids have been changed. Synthetic growth hormone releasing factors, vide infra, may be obtained using any known method; solution (wet) synthesis, solid phase synthesis, fermentation or a combination of these methods. Synthetic growth hormone releasing factors may be exact duplicates of a natural growth hormone releasing factor or they may differ by up to 20 amino acids. Growth hormone releasing factor or analogs thereof may be used in a cross-species manner. Human growth hormone releasing factor may be used, e.g., in medicine. Analogs may be obtained from their respective growth hormone releasing factor, they may be isolated from natural sources or they may be prepared by synthesis or fermentation. An example of an analog which may be used is rat $Nle^{27}$-hGRF(1-29) $NH_2$.

The growth hormone releasing factor or its analog is administered over a period of time of 10 days or more, and can be advantageously administered for a period of months to years. Administrations ranging from 2 months to 25 years may be used.

The growth hormone releasing factor or analog thereof may be administered in any manner in which it has been heretofore administered discontinuously. It may be administered neat, or it may be administered in any suitable pharmaceutical vehicle; liquid, solid or gel-like in concentrations ranging from 0.1 µg/ml to saturation, preferably 0.1 µg/ml to 1000 µg/ml in solution. It may be administered in any medium compatible with it and the patient being treated; appropriate saline solutions, albumin, serum or plasma. For example, a vehicle made of sterile water and serum albumin adjusted to a physiological pH may be used. Hydrochloric acid in dilute concentrations (e.g., $10^{-1}$ to $10^{-N}$ HCl) and lactose and ascorbic may be added to the vehicle. Human, bovine or porcine albumins may be used. For example, administration may be effected orally, intranasally, subcutaneously, intravenously or transdermally. Delayed release preparations may be used implanted under the skin of vertebrates. The growth hormone releasing factor or its analog may be microencapsulated and implanted subcutaneously in a manner standard for peptide subcutaneous implants. In oral administration it may be used as a formulation designed to protect the growth hormone releasing factor or its analog from enzymes to which it is sensitive, e.g., proteases. All of these modes of administration are known to those skilled in this art.

The present invention provides the advantage that a long acting delayed release preparation may now be used in varied cultivations—dairy to improve, e.g., milk or meat production, in fish cultivation and fowl cultivation to improve, e.g., meat production. These delayed release preparations may also be used in medicine. The invention produces beneficial results over weeks or months. Since the purpose of increasing growth hormone secretion is to accelerate growth or change body composition therapy needs to be prolonged over weeks to months, the present invention now make growth hormone releasing factor more acceptable for use in fisheries, various cultivations and medicine. Additionally, growth hormone releasing factor is now preferable for use over growth hormone since only infrequent injections will be necessary.

The continuous administration of growth hormone releasing factor or analogs thereof does not result in adverse effects to the patient. No changes in blood pressure, pulse rate, or body temperature and no side effects have been noted.

The invention possesses the following major advantages. The new concept that has been invented is that growth hormone releasing factor or an analog thereof may be administered in a constant manner and yet produce intermittent pulsatile growth hormone administration. The short-term administration of growth hormone releasing factor (6-24 hours) stimulates growth hormone secretion intermittently over the duration of the infusion rather than stimulating it through the infusion; growth hormone is stimulated in pulsatile fashion. The majority of growth hormone is secreted at the usual time of the day, i.e., during the night. However, when a supramaximal dose of growth hormone releasing factor is administered at the end of the 6 or 24 hour infusion, a reduced release of growth hormone is noted in response to the growth hormone release factor (Vance, M. L.; Kaiser, D. L.; Evans, W. S.; Furlanetto, R.; Vale, W.; Rivier, J.; Thorner, M. O., *J. Clin. Invest.*, 1985, 75, 1584–1590, and Vance, M. L.; Kaiser, D. L.; Evans, W. S.; Thorner, M. O.; Furlanetto, R.; Rivier, J.; Vale, W.; Perisutti, G.; Frohman, L. A., *J. Clin. Endocrinol. Metab.*, 1985, 60, 370–375). These observations are interpretable as a desensitization. Pulsatile growth hormone secretion could be sustained in the presence of constant growth hormone releasing factor levels, thus indicating that another factor, presumably somatostatin (although no limitation of the present invention is intended here), is involved in the pulsatile pattern of growth hormone secretion.

Other features of the invention will become apparent in the course of the following descriptions of exemplary embodiments which are given for illustration of the invention and are not intended to be limiting thereof.

Growth hormone releasing factor was administered by mechanical pump which delivered a dose of 10 ng/kg/min by the intravenous route over 14 days in 4 subjects aged 26 to 31 years. The profile of growth hormone secretion was measured over 24 hours before the initiation of the infusion, on the fourteenth day of the infusion, and two weeks after stopping the infusion. The results showed that there was augmented growth hormone secretion at 14 days of the infusion, that the subjects could respond with normal or accentuated responses to a supramaximal dose of growth hormone releasing factor and most importantly, that there was a rise in serum Insulin Growth Factor-1 (IGF-1) level, which is a marker of biological activity of growth hormone.

EXAMPLES

Intravenous infusions of growth hormone releasing factor. Studies have been performed on normal young men who were given incremental doses of growth hormone releasing factor-40 for 90 minutes increasing from 1 to 3.3 to 10 to 33 ng/kg/min Webb et al, *J. Clin. Invest.*, 1984, 74, 96–103). In addition, studies using 6 hours infusions of 1, 3.3 and 10 ng/kg/min were done (Vance et al, *J. Clin. Endocrinol. Metab.*, 1985, 60, 370–375). In this study it was observed that a supramaximal bolus injection of growth hormone releasing factor-40 (GRF-40) given at the end of the infusion, stimulated a growth hormone response that was inversely related to the 6 hour infusion dose suggesting either desensitization or depletion of a finite releasable pool.

In a most recent study the 6 hour infusion was repeated but insulin was given at the end of the infusion to provide an alternate stimulus (hypoglycemia) for growth hormone secretion compared to hypoglycemia after vehicle infusion. Thus (1) partial homologous desensitization to growth hormone releasing factor occurs; and (2) hypoglycemia stimulates growth hormone secretion by non-growth hormone release factor mechanisms. Next 24 hour infusions of growth hormone releasing factor were performed and the growth hormone and growth hormone releasing factor secretory profile of a patient were studied with ectopic growth hormone releasing factor secretion (Vance et al, *J. Clin. Invest.*, 1985, 75, 1584–1590). In this patient growth hormone secretion was pulsatile despite continuously elevated immunoreactive growth hormone releasing factor levels. To determine if pulsatile growth hormone secretion is maintained in normal subjects, vehicle or growth hormone releasing factor-40, 2 ng/kg/min, was administered to six healthy young men for 24 hours and gave a supramaximal intravenous bolus dose of growth hormone releasing factor-40, 3 $\mu$g/kg after 23.5 hours of infusion. Growth hormone releasing factor-40 infusion resulted in greater growth hormone secretion than did vehicle infusion and pulsatile growth hormone secretion was maintained throughout the growth hormone releasing factor-40 infusion. Not only was pulsatile growth hormone secretion maintained during growth hormone releasing factor-40 infusion, but there was augmentation of naturally occuring growth hormone pulses, which is in contrast to the effect of Gonadotropin Releasing Hormone on Gonadotropin secretion.

Obviously, numerous modifications and variations to the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A method for increasing growth hormone secretion in a human patient, which comprising continuously, intravenously administering a human growth hormone releasing factor to said patient for a period of ten days, at a dosage level of 1.0 mg/kg/min. to 100 mg/kg/min.

* * * * *